United States Patent [19]

Marshall

[11] 4,171,485
[45] Oct. 16, 1979

[54] APPARATUS FOR ANALYZING THE SPECTRAL DATA IN AN ELEMENTAL ANALYZER MEASURING GAMMA RAYS ARISING FROM NEUTRON CAPTURE IN BULK SUBSTANCES

[75] Inventor: J. Howard Marshall, Pasadena, Calif.

[73] Assignee: MDH Industries, Inc., Monrovia, Calif.

[21] Appl. No.: 835,807

[22] Filed: Sep. 22, 1977

[51] Int. Cl.² .................. G01N 23/00; G01V 5/00
[52] U.S. Cl. ............................... 250/359; 250/255
[58] Field of Search ............... 250/358, 359, 360, 390, 250/391, 392, 253

[56] References Cited

U.S. PATENT DOCUMENTS

| | | | |
|---|---|---|---|
| 3,053,388 | 9/1962 | Tittle | 250/359 |
| 3,676,675 | 7/1972 | Ransohoff et al. | 250/453 |

Primary Examiner—Alfred E. Smith
Assistant Examiner—Janice A. Howell
Attorney, Agent, or Firm—Arthur V. Doble

[57] ABSTRACT

An apparatus for analyzing the spectral data in an elemental analyzer measuring gamma rays arising from neutron capture in bulk substances is disclosed. The formation of optimally-weighted linear sums of the number of counts in various portions of the energy spectrum of neutron-capture gamma rays improves measurement accuracy in an apparatus for on-line elemental analysis of bulk substances. Within the apparatus, the analyzed bulk substance is exposed to neutrons, and neutron capture generates prompt gamma rays therefrom. A detector interacts with some of these gamma rays to produce electrical signals used to convert their energy spectrum to digital form by pulse-height analysis. A small computer uses this digitized spectrum to construct the weighted linear sums corresponding to at least one interesting element. Generally, several elements are measured, and the computer forms ratios between the elemental sums to provide relative concentration measurements which are independent of absolute counting rates. The instrument also contains a calibration plug to verify performance, a digital data link to allow the computer to be remote from the gamma-ray detector and devices to display the results of the measurement and/or to communicate them to external equipment. Measurement of an element principally present in the instrument structure permits the computer to correct the measurement of an interesting element in the bulk substance for its presence in the structure.

21 Claims, 3 Drawing Figures

FIGURE 3   BLOCK DIAGRAM — DATA-ANALYSIS EQUIPMENT

APPARATUS FOR ANALYZING THE SPECTRAL DATA IN AN ELEMENTAL ANALYZER MEASURING GAMMA RAYS ARISING FROM NEUTRON CAPTURE IN BULK SUBSTANCES

BACKGROUND OF THE INVENTION

1. Field of the Invention

This invention generally relates to nuclear meters, and particularly to an apparatus or a method for analyzing the spectral data and for reducing the deleterious effects caused by gamma rays from interfering elements or other effects in a neutron-capture-based elemental analyzer for on-line measurement of bulk substances.

2. Description of the Prior Art

The rising cost of fuels, coupled with the need to avoid atmospheric pollution when burning them, has led to the requirement that their composition be known at various points in the fuel-preparation cycle. For example, because of the scarcity of low-sulfur crude oils and the cost of sulfur removal, the value of fuel oil increases significantly as its sulfur content becomes lower, indicating that accurate fuel-oil blending to a fixed sulfur level consistent with allowable amounts of pollution is both cost effective and efficient utilization of increasingly-scarce hydrocarbons. Furthermore, precise knowledge of the heat content of fuel oil allows furnaces and boilers to be operated in a more efficient manner. In addition, knowledge of the amount of sulfur and other contaminants such as vanadium and nickel in various hydrocarbon streams can help prevent the poisoning of catalysts used in oil refineries, avoiding costly shut downs.

In the case of coal, sulfur content is generally higher than that of oil, making the pollution problem even more severe. As a result, expensive coal-cleaning plants, stack-gas scrubbers and precipitators are necessary, all of which can be operated more efficiently if the coal composition is known on a real-time on-line basis. Efficient boiler operation also benefits from this composition measurement, and knowing the composition of the ash in the coal can be used to avoid boiler slagging.

Because these composition measurements have to be made on inhomogeneous substances with high mass flow rates and variable compositions, the measurement should continuously reflect the average composition of the bulk substance. Response times should be fast enough to permit effective process control, which generally implies a speed of response ranging from a few minutes up to an hour.

A technique which can satisfy these requirements can often be used in applications which do not involve fuels or their derivatives. For example, it could measure the nitrogen content of wheat in order to determine the amount of protein present, which in turn is related to food value. Thus, the measurement of fuels is illustrative only and is not essential to this invention, which applies to all measurements of bulk substances by the techniques to be described hereinafter.

Several methods for composition measurement are known in the prior art, the most obvious one being sampling followed by chemical analysis. This technique provides most present data on the composition of various bulk substances. Unfortunately sampling is inherently inaccurate because of the lack of homogeneity of bulk materials, and large continual expenditures for manpower, sampling devices and chemical-analysis equipment are required to provide response times which at best could approach one hour. These disadvantages lead to the consideration of other techniques which are faster, more subject to automatic operations and more of an on-line continuous bulk measurement.

One technique often used in industrial environments for elemental analysis involves X-ray fluorescence. This technique relies on the fact that each atom emits X rays with distinct and well-known energies when external radiations disturb its orbital electrons. Unfortunately, sulfur, which is an interesting element from the standpoints of air pollution and catalyst poisoning, emits mostly 2-keV X rays, which can only traverse about 0.1 mm of a typical fuel. Iron, which is one of the elements generating the highest-energy X rays in coal, produces mostly a 6-keV X ray, which also cannot escape from any appreciable amount of coal or other nongaseous fuel. Thus, the use of X-ray fluorescence for other than gaseous materials requires either the preparation or the vaporization of a sample in an atmosphere which does not confuse the measurement. In either case, a difficult sampling and sample-preparation problem compounds the errors associated with X-ray fluorescence itself.

A second technique usually involving X rays which are more penetrating is X-ray absorption. In this case one measures the differences in the absorption or scattering of X-rays caused by changes in the amounts of certain elements. In the case of relatively-pure hydrocarbons such as refined fuel oil, this technique can provide a useful measurement of sulfur content because sulfur at X-ray energies near 22 keV can have a predominant effect on the X-ray absorption. This predominance, however, is dependent on the lack of most of the metals which are present in coal and may also be present in oil. In addition, 22-keV X rays only penetrate about 2 mm in most non-gaseous fuels, making sampling still a requirement. Moreover, this technique is generally limited to measuring only one of several potentially interesting elements, and the measurement of the relative amounts of many different elements in a complex mixture such as coal becomes difficult.

Nonetheless, nuclear techniques in general remain attractive because they often can be automated and in principal do not require actual manipulation of the bulk material itself. The problems with X-ray fluorescence and absorption arise partly because the associated radiations are not sufficiently penetrating. However, because the energetic gamma rays produced by the capture of thermal neutrons will penetrate over 100 mm of most fuels, an analysis technique based on them can provide an accurate, continuous, on-line measurement of the elemental composition of bulk substances without sampling.

This technique is based on the fact that almost all elements when bombarded by slow neutrons capture these neutrons at least momentarily and form a compound nucleus in an excited state. Usually the prompt emission of one or more gamma rays with energies and intensities which are uniquely characteristic of the capturing nucleus dissipates most of this excitation energy. Because these prompt gamma rays often have energies in the 2- to 11-MeV range, they can penetrate substantial quantities of material to reach a gamma-ray detector and its associated electronics which provide a measurement of their energy spectrum. Thus, for those isotopes with significant capture cross sections and prominent gamma-ray lines, measurement of the number of prompt gamma rays present at various energies can be used to determine in an on-line, real-time basis the quantity of most of the elements present in bulk substances, which can be flowing through the analyzer.

Although this technique has been used in the laboratory under controlled conditions, its implementation in an automatic, on-line instrument placed in an industrial environment presents unique problems. One of these problems result from the need to measure accurately the concentration of one element in the presence of varying concentrations of other elements. Because most elements produce capture gamma rays, the measured energy spectrum can become complex when several elements are present in the bulk substance being analyzed or in structural materials exposed to the neutrons. Moreover an interesting element may be present in both the substance being analyzed and in the structural materials, leading to the problem of distinguishing between detected gamma rays from these two sources.

In addition most elements produce many gamma rays with differing energies, and each one of the energetic gamma rays produces in turn three peaks in the pulse-height spectrum because of the escape of none, one or two positronannihilation photons. Because of the finite energy resolution of the detector, these peaks may interfere with each other, so that in the composite spectrum of a low-resolution detector such as NaI(Tl) few peaks arise purely from a single gamma ray, and simply counting events near a line from an interesting element seldom produces an accurate measurement of the concentration of that element.

This problem becomes more complex because these peaks ride on a slowly-varying continuum mostly generated by Compton scattering in materials both within and outside of the detector. Although the contribution of the detector to the continuum yields a fixed ratio of a peak height to the Compton continuum, the contribution of the medium outside of the detector depends on its density and neutron-moderation properties. Additionally pulse pileup, gamma rays from the source and shielding materials, and neutron reactions in the detector and its housing can add to the continuum and can possibly also produce undesirable peaks in the spectrum.

Even if the peaks are separated from the continuum and after various interferences are resolved, absolute counting rates are still not useful directly. For example, an isotopic neutron source will decay. Additionally the predominance of hydrogen and trace elements with large neutron-capture cross sections in the capture of neutrons makes the absolute rates overly sensitive to the amount of these elements present. Moreover, the size of the neutron cloud, determined by the moderating properties and density of the region around the source and detector, effects absolute rates and the peak-to-Compton ratios.

Prior-art instruments used for measuring the sulfur content of coal attempted to overcome these problems by dividing the energy spectrum into two regions. One of these regions included the peak near 5.43 MeV produced by gamma rays from sulfur, and the other region was immediately adjacent to the first region. By subtracting the number of counts in the second region from the number of counts in the first region, the resulting difference could be made relatively independent of the amount of iron present in the coal.

However, this technique was effective only over a small range of elemental concentrations and provided no immunity for changes in other elements such as nitrogen. In addition only the concentration of sulfur could be measured, and errors in this measurement arose when the carbon-hyrogen ratio in the coal changed. Thus, the prior-art technique for analyzing the spectral data was too simplistic for a general-purpose elemental analyzer, which must perform accurately even if the composition of the bulk substance changes.

SUMMARY OF THE INVENTION

In distinction to the prior-art instruments with only two relatively-narrow regions in the energy spectra, this invention provides for defining many energy regions covering most of the range of energies of the capture gamma rays, with the energy windows grouped selectively about peaks carrying significant information. A digital computer or microprocessor then constructs weighted linear sums of the count rates in these windows to increase selectively the sensitivity to one element while decreasing the sensitivity to other interfering elements. Several such sums with different weighting coefficients yield outputs which are indicative of the relative concentrations of different elements. This type of analysis eliminates in the following manner most of the interferences between elements capturing significant fractions of the thermal neutrons and also corrects automatically for the slowly-varying continuum. Normalization to one element or group of elements removes the problems inherent in using absolute counting rates.

For each interesting element, Q, the computer constructs an elemental sum, $C_Q$, using the number of counts, $R_j$, in the energy window designated by the subscript j. This elemental sum can be written as $$C_Q = \sum_{j=1}^{N} Q_j R_j, \quad (1)$$

where the energy spectrum has been divided into N energy windows, and where $Q_j$ is the weighting factor associated with the element Q and the energy window j. Similarly, other elemental sums using weighting factors $P_j$, $S_j$, etc. will determine the concentrations $C_P$, $C_S$, etc., of other elements designated by P, S, etc. using the same counting rates $R_j$. Thus, the same data can be manipulated in different ways to obtain simply the concentrations of different elements.

Because the values of the elemental sums are proportional to source strength, counting time, etc., as well as being related to the concentration of the interesting element, their absolute scaling cannot be significant, and a multiplicative constant could be applied to all of the $Q_j$, simply multiplying $C_Q$ by the same amount. Thus, ultimately the ratios between the elemental sums and the elemental sum for a specific reference element (or a weighted sum of reference elements) should be formed, and the multiplicative constant can then be chosen to give the correct ratio for a known case. Because this constant cannot effect the procedure for choosing the weighting factors in an optimum fashion, all of the elemental sums can be normalized to one for a standard composition used for the determination of the weighting factors.

The number of counts, $R_j$, in a given energy window consist of those counts, $A_j$, from the interesting element, Q, and the sum of counts, $V_{ij}$, from the M background sources, each of which is designated by a subscript i. If the elemental sum, $C_Q$, is to be proportional to the amount of the element Q with zero offset, and, if the number of counts A, from the interesting element is also proportional to its concentration over the range of interest, then the normalization and offset conditions imply for the standard composition that $$\sum_{j=1}^{N} Q_j A_j = 1 \tag{2}$$

and tha $$\sum_{i=1}^{M} \sum_{j=1}^{N} Q_j V_{ij} = 0, \tag{3}$$

where $$R_j = A_j + \sum_{i=1}^{M} V_{ij}. \tag{4}$$

Consideration of the various types of errors in such a measurement leads to a determination of the optimum values for the weighting factors, $Q_j$. The error sources used in the optimization procedure may include statistical fluctuations, variations in the concentrations of the various sources of background, and the effects of electronic drifts in the boundaries between the energy windows.

The detection of an event in a given energy window is a random process for which the mean rate and the standard deviation can be predicted, but the precise detection time remains a random variable. For such a process the standard deviation equals the square root of the number of detected events. Thus, if $r_{ij}$ is the counting rate from element i in energy window j and if T is the counting interval, then the standard deviation, $\sigma_{ij}$, in this number is given by $$\sigma_{ij} = \sqrt{r_{ij} T}. \tag{5}$$

Because the various sources of counts in the energy window j are statistically independent, the standard deviation of the total number of counts in the window j, $\sigma_j$, becomes $$\sigma_j^2 = \sigma_{Aj}^2 + \sum_{i=1}^{M} \sigma_{ij}^2 = \left[ a_j + \sum_{i=1}^{M} r_{ij} \right] T, \tag{6}$$

where $a_j$ is the counting rate for the interesting element. Similarly, because the number of counts in different energy windows are also statistically independent and the $Q_j$ are constants without statistical fluctuations, the standard deviation, $\sigma_Q$, in $C_Q$ defined by equation 1 becomes $$\sigma_Q^2 = \left\{ \sum_{j=1}^{N} Q_j^2 \left[ a_j + \sum_{i=1}^{M} r_{ij} \right] \right\} T, \tag{7}$$

where $$C_Q = \sum_{j=1}^{N} Q_j \left[ a_j + \sum_{i=1}^{M} r_{ij} \right] T. \tag{8}$$

In addition to the above statistical errors, various systematic effects, which are independent of the counting interval, contribute to errors in the concentration measurements. These error sources include variations in the interfering background and drifts in the thresholds defining the energy windows.

Equation 3 permits the offset resulting from interferences to be zero for one particular composition. If the $V_{ij}$ in this equation are proportional to the concentration of the various background-producing elements, then scaling all of these elements upward or downward by the same factor still leaves the offset zero. Thus, the case leading to potentially-significant offset errors is the one where the changes in the concentrations of the various background elements are uncorrelated with one another.

The quantity defined by $$D_i = \sum_{j=1}^{N} Q_j V_{ij}, \tag{9}$$

represents the contribution of the element designated by the subscript i to the offset term. For the reference composition used for optimization, equation 3 implies that $$D_Q = \sum_{i=1}^{M} D_i = 0. \tag{10}$$

Now if $k_i$ represents the concentration of element i for the reference composition of $k_i + \delta k_i$ represents the concentration of i for a different composition, then for this new composition $D_i$ becomes $D_i'$ given by $$D_i' = \left( 1 + \frac{\delta k_i}{k_i} \right) D_i, \tag{11}$$

and the total systematic error, $D_Q'$, then becomes $$D_Q' = \sum_{i=1}^{M} \left( \frac{\delta k_i}{k_i} \right) D_i. \tag{12}$$

In the event that the $\delta k_i / k_i$ are independent random variables, the mean-square value for the systematic error, $\overline{D_Q^2}$, becomes $$\overline{D_Q^2} = \sum_{i=1}^{M} \overline{\left( \frac{\delta k_i}{k_i} \right)^2} \left[ \sum_{j=1}^{N} Q_j V_{ij} \right]^2. \tag{13}$$

For the special case where the mean-square relative deviations, $\overline{(\delta k_i / k_i)^2}$, for all of the background-producing effects are unity, then $$D_Q^2 = \sum_{i=1}^{M} \left[ \sum_{j=1}^{N} Q_j V_{ij} \right]^2. \tag{14}$$

Although equation 3 implies that the offset can be made to vanish for a specific composition, equation 12 shows that for other compositions small offsets may exist. Drifts in the boundaries of the energy windows after the $V_{ij}$ have been measured and the $Q_j$ have been chosen can also lead to a non-zero offset, even if the composition has not changed.

Consider the boundary at energy $T_j$ between window j-1 and j. If the differential pulse-height distribution from element i is given by $dN_i/dE$, then $$V_{ij} = \int_{T_j}^{T_{j+1}} \left(\frac{dN_i}{dE}\right) dE, \quad (15)$$

and $$\frac{\partial V_{ij}}{\partial T_j} = -\frac{dN_i}{dE}\bigg|_{T_j}. \quad (16)$$

Similarly $$\frac{\partial V_{ij-1}}{\partial T_j} = \frac{dN_i}{dE}\bigg|_{T_j} = -\frac{\partial V_{ij}}{\partial T_j}, \quad (17)$$

so that $$\frac{\partial D_i}{\partial T_j} = (Q_{j-1} - Q_j)\frac{dN_i}{dE}\bigg|_{T_j} \quad (18)$$

and $$\frac{\partial D_Q}{\partial T_j} = (Q_{j-1} - Q_j)\sum_{i=1}^{M}\frac{dN_i}{dE}\bigg|_{T_j}. \quad (19)$$

If $\delta T_j$ represents a small error in the threshold $T_j$, then the corresponding error in the offset is given by $$\delta D_Q = \delta T_j (Q_{j-1} - Q_j)\sum_{i=1}^{M}\frac{dN_i}{dE}\bigg|_{T_j}. \quad (20)$$

If a two-parameter stabilizer for the pulse-height analyzer makes it unlikely that the drifts in the various energy thresholds will be correlated with each other, the mean-square deviation in the offset, $\overline{\delta D_Q^2}$, becomes $$\overline{\delta D_Q^2} = \sum_{j=1}^{N}\overline{\delta T_j^2}\left[(Q_{j-1}-Q_j)\sum_{i=1}^{M}\frac{dN_i}{dE}\bigg|_{T_j}\right]^2, \quad (21)$$

where $\overline{\delta T_j^2}$ is the mean-square drift of the threshold $T_j$, and where the upper boundary for window N is at infinite energy with $Q_0$ defined as zero.

For the case where all of the $\overline{\delta T_j^2}$ are equal to $\overline{\delta T^2}$, then $$\overline{\delta D_Q^2} = \overline{\delta T^2}\sum_{j=1}^{N}\left[(Q_{j-1}-Q_j)\sum_{i=1}^{M}\frac{dN_i}{dE}\bigg|_{T_j}\right]^2 \quad (22)$$

represents the mean-square offset arising from these threshold drifts. Because a similar expression using the differential spectrum for the interesting element yields the drift in the gain factor for that element, the sum over i in equation 22 should be replaced by dN/dE, where dN/dE refers to the entire differential pulse-height distribution.

When the standard deviation from statistical fluctuations, the mean-square value of the systematic error caused by background variations and the mean-square offset arising from threshold drifts are statistically independent and have equal importance, the total error, $\overline{E_Q^2}$, associated with the measurement of the element Q is given by $$\overline{E_Q^2} = \sigma_Q^2 + \overline{D_Q^2} + \overline{\delta D_Q^2}. \quad (23)$$

Because of the normalization provided by equation 2, this total error represents the fractional error directly for the reference composition, indicating the simplification in data interpretation obtained by setting $C_Q=1$ in that case.

If two Lagrange multipliers, $2\mu$ and $2\lambda$, allow for the two constraints, then the minimum total error will result when for each of the N $Q_j$ $$\frac{\partial}{\partial Q_j}[\overline{E_Q^2} + 2\lambda C_Q + 2\mu D_Q] = 0, \quad (24)$$

which reduces to $$Q_j\left[\sum_{i=1}^{M}(V_{ij}+V_{ij}^2) + A_j\right] + \sum_{\substack{k=1\\k\neq j}}^{N} Q_k \sum_{i=1}^{M} V_{ij}V_{ij} + \lambda A_j + \mu \sum_{i=1}^{M} V_{ij} \quad (25)$$

$$Q_j\left[\sum_{i=1}^{M}(V_{ij}+V_{ij}^2) + A_j\right] + \sum_{\substack{k=1\\k\neq j}}^{N} Q_k \sum_{i=1}^{M} V_{ik}V_{ij} + \lambda A_j + \mu \sum_{i=1}^{M} V_{ij}$$

Includng the two constraints given by equations 2 and 3, this set constitutes N+2 linear equations in N+2 unknowns, which are the N $Q_j$, $\mu$ and $\lambda$. The solution of these equations yields the optimum values for the $Q_j$. This procedure can generate a separate set of weighting factors for each element of interest, allowing the same counting-rate data to be manipulated in different ways to obtain measurements of the concentrations of several elements.

The availability of concentration measurements for several elements permits the determination of the relative concentration of one or more of these elements in a manner which provides an output which is relatively immune to errors produced by unstable absolute numbers of counts arising from changing counting intervals or from varying conditions for the bulk substance being measured or the source. Because these effects tend to change the absolute number of counts for all of the elements proportionally, ratios between the number of counts for different elements become independent of these spurious effects. In particular the ratio of the individual elemental sums to a normalizing number which has been constructed by taking the appropriately-weighted sum of the elemental sums for one or more interesting elements will then be independent of the effects which change all of the absolute number of counts by the same factor.

The best choice for the normalizing number depends on the use for the instrument. For example, if the instrument should read out the fraction by weight of an element in dry coal, the normalizing rate should reflect the total composition of dry coal. Similarly, if the output should be in such units as the amount of an element per unit heat output from a given fuel, then the normalizing factor should reflect the calorific value of the fuel. The normalizing factor could also reflect elements of primary importance, such as carbon in coal or hydrogen and carbon in oil.

A second application for the elemental sums arises when an interesting element is present in both the instrument structure and in the bulk substance being analyzed. If the structural material also contains an element which is not present in the analyzed substance in substantial quantities, and if the amount of this second element (or elements) bears a fixed relationship in the structure to the amount of the interesting element, then the appropriate fraction of the elemental sum from the second element can be subtracted from the elemental sum for the first element. The resultant reduced elemental sum then represents the concentration of the interesting element in the analyzed substance only.

The present invention has several features of novelty over the known prior art, including the use of a computer to process the sprectral data produced by neutron-capture gamma rays in an on-line elemental analyzer in a manner that provides an elemental-concentration measurement with enhanced accuracy.

It is an object of this invention to provide an improved apparatus for measuring the energy spectrum of neutron-capture gamma rays and for processing the resultant spectral data to avoid errors for interfering signals in the measurement of the concentration of one or more interesting elements.

It is an additional object of this invention to provide an improved apparatus for indicating the concentration of one or more interesting elements in a bulk substance.

It is a further object of this invention to provide a concentration measurement which is independent of absolute counting rates or counting intervals.

It is another object of this invention to correct the measured amount of an element present in the analyzed bulk substance for the presence of that element in the instrument structure.

It is also an object of this invention to provide a standard analyzable substance for the determination of the parameters used in the processing of the spectral data.

For a better understanding of the present invention, together with other and further objects thereof, reference is made to the following description taken in connection with the accompanying drawings in which preferred embodiments of the invention are illustrated, the scope of the invention being pointed out and contained in the appended claims.

DESCRIPTION OF THE PREFERRED EMBODIMENTS

Figure 1:
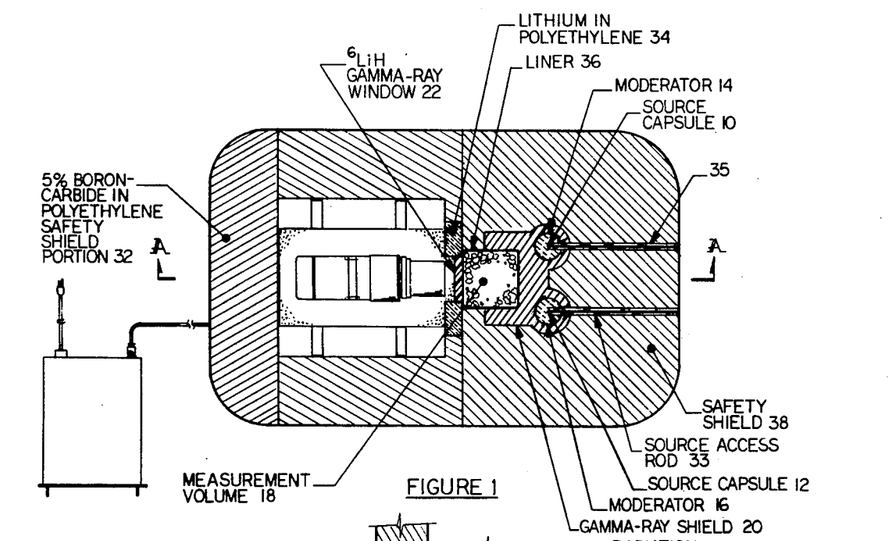
FIG. 1 shows a cross-sectional view of a meter for the elemental analysis of coal. Included therein are the gamma-ray detector, the sensor electronics and the display console, in which are contained a preferred embodiment of this invention.
Figure 2:
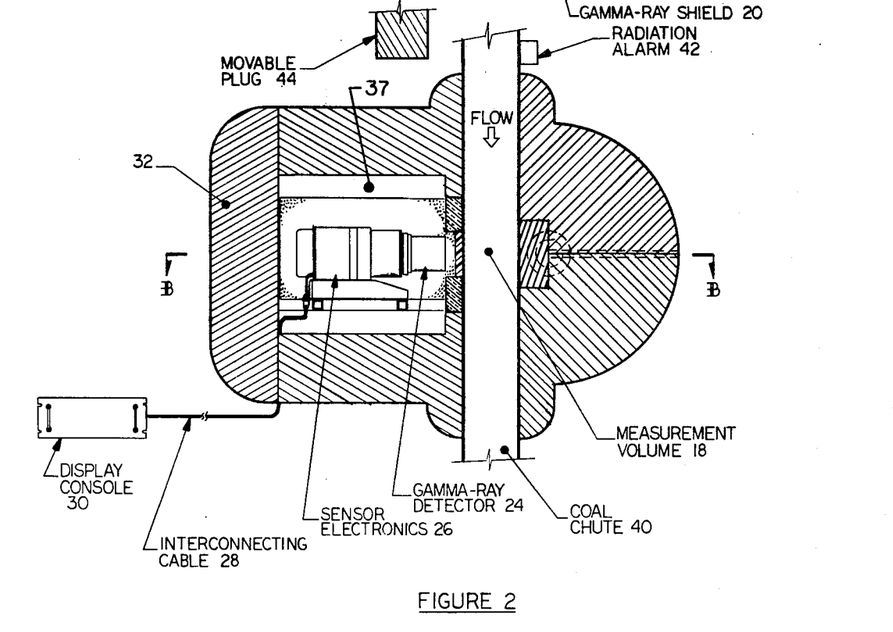
FIG. 2 shows further details of the same instrument as that shown in FIG. 1, but in this case the section view has been taken along the line A—A in FIG. 1. The line B—B of FIG. 2 shows the sectioning line used for producing FIG. 1.
Figure 3:
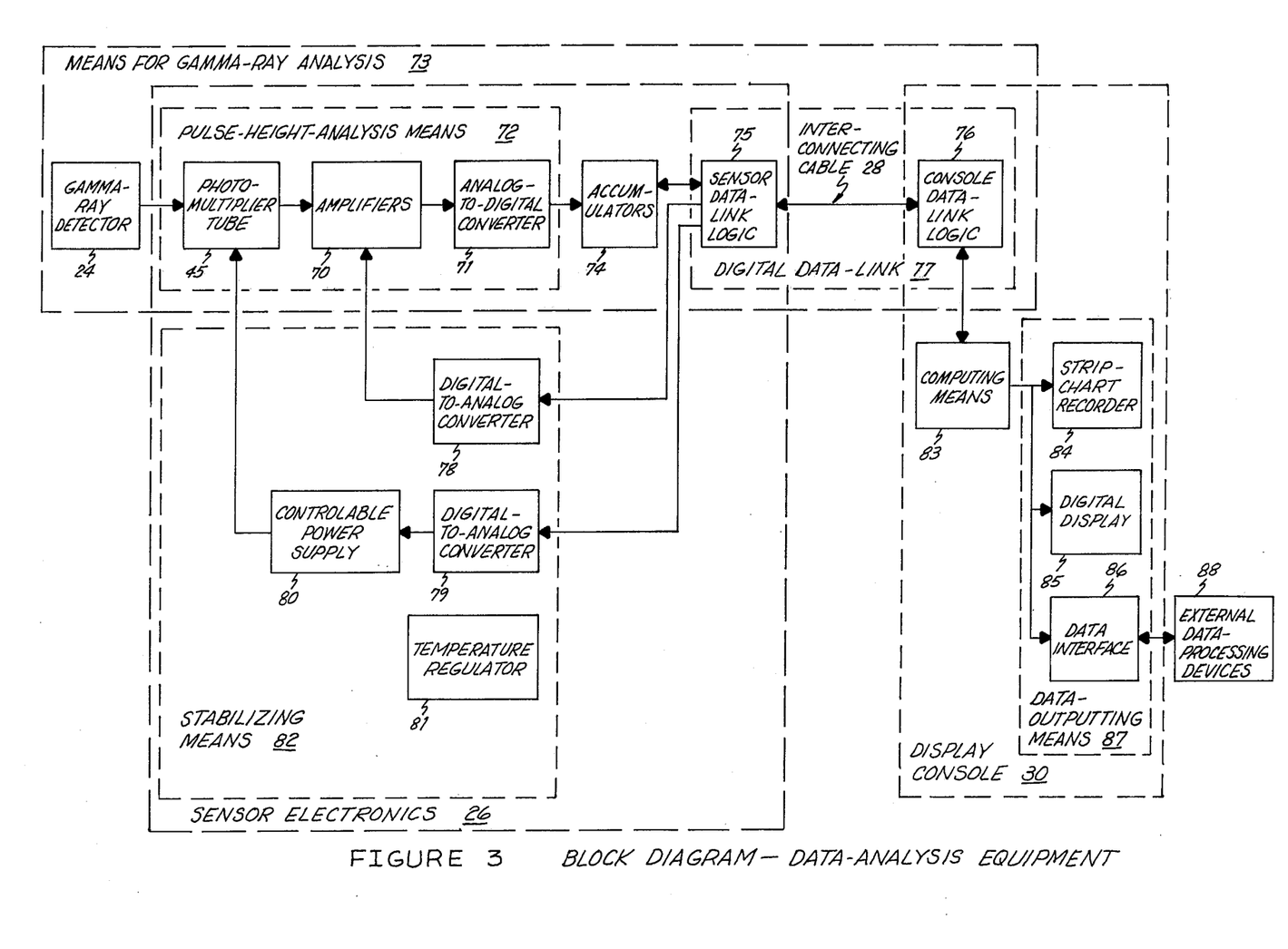
FIG. 3 shows the functional blocks of the data-analysis equipment, which is mostly contained in the sensor electronics and display console shown in FIGS. 1 and 2, and provides more detail of a preferred embodiment of this invention.

The application of these methods to the elemental analysis of coal forms one of the preferred embodiments of this invention, as shown in FIGS. 1, 2 and 3. Other embodiments involve the on-line measurement of coal-water mixtures, coal-oil mixtures, crude oil, fuel oil, gasoline, wheat and most other bulk substances containing some hydrogen. Thus, the portions of the preferred embodiment shown in FIGS. 1, 2 and 3 which are specific to the measurement of coal are illustrative only and are not intended to limit the scope of this invention.

The instrument includes means for containing the bulk substance to be analyzed, which may flow through the instrument in order to provide a continuous, on-line measurement of bulk composition. In the embodiment shown in FIGS. 1 and 2, this means consists of the centrally-located measurement volume 18, in which the coal being analyzed is confined. Measurement volume 18 is the region throughout which the composition measurement takes place. Coal passing through the coal chute 40 continuously fills the measurement volume 18 with a current coal sample, facilitating the desired continuous, on-line bulk measurement.

The instrument also inclues neutron-producing means fo providing neutrons. In the embodiment shown in FIG. 1, said neutron-producing means consist of two source capsules 10 and 12 containing the isotope californium-252. In other embodiments of this invention the source could contain different isotopes, such as plutonium mixed with beryllium, or could contain a neutron generator, such as that using the $^3H(d,n)^4He$ reaction. Additionally the instrument could contain one or several neutron sources, which could all be the same type or could be various combinations of source types. The neutron-producing means can be located either outside of the volume containing the bulk substance to be analyzed, as shown in FIGS. 1 and 2, or within this volume. If several neutron sources are present, some of these sourves may be within this measurement volume, while other sources are external thereto. The principles forming a part of this invention apply to all of these variations of the embodiment shown in FIGS. 1 and 2.

In this embodiment neutron moderators 14 and 16 surround the source capsules 10 and 12 in order to reduce neutron energies before the neutrons enter the measurement volume 18. A gamma-ray shield 20 then surrounds the moderators 14 and 16 to absorb gamma rays produced by the source and the moderators and to provide a material with low neutron absorption through which neutrons can diffuse away from the source. The use of the moderators and gamma-ray shield is also not essential to this invention, and their use in the embodiment shown in FIGS. 1 and 2 is not intended to limit the scope of the invention.

In the preferred embodiment shown in FIGS. 1 and 2, the neutron sources 10 and 12 are outside of the measurement volume 18, indicating that most neutrons will not enter the measurement volume 18. In order to control these unused escaping neutrons to avoid a radiation hazard and background in the measured energy spectrum, the preferred embodiment shown in FIGS. 1 and 2 includes the $^6LiH$ gamma-ray window 22, the boron-doped-polyethylene safety shields 38 and 32 with the source access rods 33 and 35, the lithium in polyethylene 34 and the liner 36 for the measurement volume 18. The existence of these neutron-absorbers in the preferred embodiment of FIGS. 1 and 2 is not intended to limit the scope of this invention.

In order to avoid a radiation hazard from escaping neutrons when the measurement volume 18 is empty, in the preferred embodiment the shield 32 on the detector side of the measurement volume 18 has been placed behind the sensor electronics 26 such that the gamma-ray detector 24 and the sensor electronics 26 are located within a chamber 37 in the neutron absorber. Even in this configuration some scattered radiation can leave the top and the bottom of the coal chute 40 passing through the measurement volume 18 when it is empty, because this region is not covered by shielding. A radiation alarm 42 and a movable plug 44 for the coal chute 40 when no coal is present provide the necessary protection to personnel when the coal chute is empty. If the movable plug 44 is constructed out of appropriate known materials, it can also become a means for instrument calibration and can be used for the determination of the weighting factors to optimize the response to interesting elements. The existence of the radiation alarm 42 and the movable plug 44 and the presence of a chamber 37 for the sensor electronics 26 in the preferred embodiment are not intended to limit the scope of this invention.

Some neutrons will diffuse through the gamma-ray shield 20 into the measurement volume 18. There hydrogen present in the coal being analyzed will moderate them further, and then they often will be captured by the various nuclei present in the analyzed coal. These neutron-capture reactions generally produce gamma rays, which travel through the measurement volume 18 and the neutron-absorbing gamma-ray window 22 and enter the gamma-ray detector 24, which in FIG. 3 is shown to be a part of the means for gamma-ray analysis 73.

In the preferred embodiment shown in FIGS. 1, 2 and 3, this detector 24 is a large NaI(Tl) crystal, although other detectors such as CsI(Tl), CsI(Na), Ge or Ge(Li) could be used in instruments incorporating the features of this invention. The invention also is not limited to the case of a single gamma-ray detector, as shown in FIGS. 1 and 2, and the principles of the invention apply equally well to instruments containing several detectors, which may be all the same type or a combination of types.

When the gamma rays interact in the gamma-ray detector 24, they produce electrical signals indicative of their energy. As shown in FIG. 3, the pulse-height-analysis means 72 and the accumulators 74 within the sensor electronics 26 convert these electrical signals into digital information, which the digital data link 77 transmits over an interconnecting cable 28 to the display console 30. The computing means 83 shown in FIG. 3 and contained within the display console 30 processes this information using the techniques of this invention. The result of this processing is information displayed by the data outputting means 87 concerning the relative concentrations of the various elements of interest in the measurement volume 18.

In the preferred embodiment shown in FIG. 3, the gamma-ray detector 24 is a doped alkali-halide crystal which scintillates in response to energy deposited by gamma rays entering it. The photomultiplier tube 45 converts these light flashes into current pulses, which the amplifiers 70 increase in magnitude sufficiently to be processed accurately by the analog-to-digital converter 71. This converter 71 defines forty amplitude windows and categorizes each detected event producing a pulse amplitude within the range of interest as belonging to one and only one such window.

For each such analyzed event, a pulse is added to the appropriate storage register in the accumulators 74, which is one manifestation of a digital means for event counting. At the end of a data-accumulation interval, the relative number of events counted by each of the forty storage registers in the accumulators 74 associated with each of the forty amplitude windows becomes a digital representation of the amplitude of the output pulses from the gamma-ray detector 24.

The use of forty amplitude windows is consistent with the finite energy resolution of a NaI(Tl) detector, but this number of windows does not constitute an essential part of this invention. Either more or fewer energy windows can be used, and a high-resolution detector such as Ge(Li) might justify considerably more amplitude windows.

In the preferred embodiment of FIG. 3, the digital information from the accumulators 74 is presented to the digital data link 77. The sensor data-link logic 75 converts the data into an appropriate form for transmission over the interconnecting cable 28 to the remotely-located display console 30. Here the console data-link logic 76 receives the transmitted data and presents them in proper form for the computing means 83.

If the computing means 83 is located near the gamma-ray detector 24, the digital data link 77 may not be necessary. As a result the digital data link 77 is not an essential part of the means for gamma-ray analysis 73.

The computing means 83 in the preferred embodiment of FIG. 3 contains a microprocessor with sufficient memory and peripheral equipment to form a small digital computer. This computer 83 generates the weighted linear sums leading to the elemental sums described above. In the preferred embodiment, the computing means 83 generates elemental sums corresponding to carbon, hydrogen, sulfur, nitrogen, silicon, iron, aluminum and titanium in order to encompass most of the elements present in coal. As error-producing signals used in the optimization process leading to the weighting factors are included pulse pileup, gamma rays from the $^{252}$Cf neutron sources 10 and 12, signals induced by neutron reactions in the detector 24, gamma rays from structural materials, and drifts in the pulse-height-analysis means 72.

In the preferred embodiment the computing means 83 also generates a normalizing factor comprising a weighted sum of the number of counts produced by each of the measured elements. After modification by small factors representing unmeasured elements which are present in the coal, this factor divides each of the measured elemental sums. The resulting quotients, which represent the fraction by weight of each of the measured elements, are presented to the data-outputting means 87 for further use. The data-outputting means 87 contains strip-chart recorders 84 for generating graphs of relative elemental concentrations versus time, digital displays 85 for showing these concentrations in numerical form, and a data interface 86 for providing digital communication to external data-processing devices 88.

Because drifts in the means for gamma-ray analysis 73 are a significant source of error, the preferred embodiment of FIG. 3 contains a stabilizing means 82. This means has a temperature regulator 81, which maintains the sensor electronics 26 and the gamma-ray detector 24 at a constant temperature. The stabilizing means 82 can also vary the gain of the pulse-height-analysis means 72 using a digital-to-analog converter 79 and a controllable power supply 80 to change the bias voltage applied to the photomultiplier tube 45. A second digital-to-analog converter 78 permits the stabilizing means 82 to change the offset of the pulse-height-analysis means 72 by way of the amplifiers 70, resulting in a two-point control of the pulse-height analysis. The computing means 83 then can cause two peaks in the gamma-ray spectrum to be centered in appropriate amplitude windows, reducing the effect of drifts in the means for gamma-ray analysis 73.

The computing means 83 can also correct the hydrogen and carbon measurements for the presence of these elements in the liner 36 based on the measurement of magnesium, which is also present in the liner 36.

What I claim as new is:

1. An improved apparatus for the on-line analysis of the composition of a bulk substance, wherein said analysis includes the production and capture of neutrons and the detection of the resulting capture gamma rays, said apparatus comprising, in combination:
   (a) means for containing the bulk substance to be analyzed;
   (b) neutron-producing means for providing neutrons which generate gamma rays by neutron-capture reactions with the nuclei in the bulk substance being analyzed, the neutron-producing means being operably associated with the means for containing the bulk substance;
   (c) means for gamma-ray analysis operably associated with the neutron-producing means and the means for containing the bulk substance being analyzed, the means for gamma-ray analysis providing for the digital measurement of the energy spectrum of the capture gamma rays;
   (d) computing means operably associated with the means for gamma-ray analysis, the computing means generating at least one weighted sum of the numbers of events found in specific portions of the energy spectrum of the capture gamma rays, with weighting factors being chosen to enhance the accuracy in the measurement of at least one element in the presence of varying concentrations of other elements; and
   (e) data-outputting means operably associated with the computing means for converting the weighted sum into an indication of the concentration of the measured element;
   whereby the statistical and systematic errors in the concentration measurement are minimized in an optimal fashion.

2. The apparatus of claim 1, above, wherein the means for gamma-ray analysis comprises:
   (a) a gamma-ray detector which produces at its output electrical signals indicative of the gamma-ray energies;
   (b) pulse-height-analysis means operably associated with the output of the gamma-ray detector, said means producing at its output a digital signal indicative of the magnitude of the electrical signal generated by the gamma-ray detector in response to a detected gamma ray; and
   (c) means for event counting operably associated with the output of the pulse-height-analysis means, the means for event counting determining the number of events producing digital signals at the output of the pulse-height-analysis means corresponding to a multiplicity of defined ranges of energy losses within the gamma-ray detector;
   whereby the energy spectrum of the detected gamma rays is converted into a form suitable for digital data processing.

3. The means for gamma-ray analysis of claim 2, above, further comprising a digital data link operably associated with the output of the means for event counting, the digital data link transmitting the digital spectral data to the computing means; whereby the computing means need not be in the immediate vicinity of the gamma-ray detector.

4. The apparatus of claim 2, above, wherein the gamma-ray detector comprises a doped alkali-halide scintillating crystal.

5. The apparatus of claim 1, above, wherein the weighting factors used in the weighted sum generated by the computing means have also been chosen to minimize errors caused by drifts in the boundaries of the energy intervals used in the digital measurement of the energy spectrum of the capture gamma rays.

6. The apparatus of claim 1, above, wherein the weighting factors used in the weighted sum generated by the computing means have also been chosen to minimize errors caused by pulse pileup.

7. The apparatus of claim 1, above, wherein the weighting factors used in the weighted sum generated by the computing means have also been chosen to minimize errors caused by gamma rays from the neutron source.

8. The apparatus of claim 1, above, wherein the weighting factors used in the weighted sum generated by the computing means have also been chosen to minimize errors caused by neutron-induced signals.

9. The apparatus of claim 1, above, wherein the weighting factors used in the weighted sum generated by the computing means have also been chosen to minimize errors caused by gamma rays from structural materials used in the means for containing the bulk substance to be analyzed.

10. The apparatus of claim 1, above, wherein the weighting factors used in the weighted sum generated by the computing means have also been chosen to produce a total contribution equal to zero for all interfering effects under at least one set of conditions.

11. The apparatus of claim 1, above, wherein the computing means generates a multiplicity of weighted sums corresponding to a multiplicity of elements.

12. The apparatus of claim 11, above, wherein the weighted sum corresponding to one element is divided by a weighted sum of the weighted sums corresponding to one or more effects;
    whereby the concentration measurement is normalized to be independent of absolute counting rates.

13. The apparatus of claim 11, above, wherein the computing means determines the amount of a first element present in the structure of the instrument by constructing a weighted sum corresponding to a second element present in the structure whose concentration in the structure bears a known relationship to the first element.

14. The apparatus of claim 13, above, wherein the computing means corrects the measurement of the concentration of the first element in the bulk substance to be analyzed for the amount of that element present in the instrument structure using the weighted sum computed for the second element present in the structure.

15. The apparatus of claim 1, above, further comprising means for instrument calibration, said means comprising known amounts of the various elements present in the bulk substance to be analyzed;

whereby the weighting factors can be determined based on the measured instrument response to known conditions.

16. The apparatus of claim 1, above, wherein the data-outputting means comprises a strip-chart recorder.

17. The apparatus of claim 1, above, wherein the data-outputting means comprises a digital display of the concentration of at least one element.

18. The apparatus of claim 1, above, wherein the data-outputting means comprises an interface with other data-processing devices.

19. The apparatus of claim 1, above, further comprising stabilizing means operably associated with the means for gamma-ray analysis, the stabilizing means increasing the accuracy of the digital measurement of the energy spectrum of the capture gamma rays.

20. The apparatus of claim 19, above, wherein the stabilizing means causes one or more outputs of the means for gamma-ray analysis to correspond to known gamma-ray energies.

21. The apparatus of claim 19, above, wherein the stabilizing means comprises a temperature regulator.

* * * * *